United States Patent [19]

Story

[11] Patent Number: 5,925,071
[45] Date of Patent: Jul. 20, 1999

[54] METHOD AND APPARATUS FOR RIDDING THE HUMAN BODY OF PATHOGENS

[76] Inventor: Craig W. Story, Suite 319, 120 E. Lake St., Sandpoint, Id. 83864

[21] Appl. No.: 08/870,747

[22] Filed: Jun. 6, 1997

[51] Int. Cl.[6] ..................................................... A61N 1/18
[52] U.S. Cl. ............................................... 607/72; 607/76
[58] Field of Search ................................. 607/72, 73, 74, 607/76, 46, 47

[56] References Cited

U.S. PATENT DOCUMENTS

| | | | |
|---|---|---|---|
| 4,509,520 | 4/1985 | Dugot | 607/76 |
| 4,924,880 | 5/1990 | O'Neill et al. | 607/76 |

Primary Examiner—Scott M. Getzow
Attorney, Agent, or Firm—Claude A. S. Hamrick; Oppenheimer W. Donnelly

[57] ABSTRACT

Briefly, a preferred embodiment of the present invention includes a low-voltage power supply, hardware including a microprocessor, a signal generator controlled by the microprocessor, and a pair of probes for making electrical contact to the body. In addition, suitable software is provided for enabling the microprocessor to control operation of the system. In accordance with this embodiment, voltages at a predetermined level are applied to the probes at oscillating frequencies which periodically change from a frequency of approximately 70 kHz at the low end to approximately 880 kHz at the high end in steps of approximately 1 kHz. Preferably, this system is programmed to repeat the cycle several times with brief respites between each cycle.

11 Claims, 7 Drawing Sheets

METHOD AND APPARATUS FOR RIDDING THE HUMAN BODY OF PATHOGENS

BACKGROUND OF THE INVENTION

1. Field of the Invention

The present invention relates generally to methods and apparatus for the electrical treatment of the human body, and more particularly to a means and process for applying electrical current to the body at frequencies known to be related to particular pathogens, with the ultimate result that such pathogens are rid from the body.

2. Discussion of the Prior Art

It has long been known that the application of electrical current through the body influences the circulatory system, metabolism, glandular activities, muscular activities, secretion of digestive juices of the internal organs, and principally the nerve system of the human body. It is also known that reflexes of the autonomous nerve system control all functions within the human body, and that the majority of diseases are caused by the abnormal functioning of the autonomous nerves. This is evidenced by the presence of natural negatively charges electrons in the cells of the body. These electrons are non-organic and non-dissipating and have an extraordinary ability to exist in a state of suspended animation in the cells of the body. Excitation of the sympathetic nerves of the skin causes depolarization resulting in increased conductivity of the affected tissue.

Similarly, since it is known that most human pathogens, including the related molds, bacteria, viruses, yeasts, parasites, tapeworms and mites, react to electrical signal frequencies in the range of 70 kHz to 880 kHz (see "The Cure for All Diseases" by Hulda Regehr Clark, Ph.D., N.D., published by Promotion Publishing, San Diego, Calif., pages 576–580), it is possible to identify such pathogens present in the human body utilizing available instrumentation. This being the case, it has now been recognized that, by applications of electrical current oscillating at specific frequencies, undesirable pathogens within the body can be eliminated allowing the body to "heal" itself, gain strength, and subsequently resist recurrence of the pathogens.

SUMMARY OF THE INVENTION

It is therefore a principal objective of the present invention to provide a novel method and apparatus for exciting human body tissues at frequencies known to interfere with and ultimately cause self-destruction of human pathogens.

Another objective of the present invention is to provide an apparatus and method of the type described which is relatively inexpensive to both acquire and use.

Still another objective of the present invention is to provide an apparatus and method of the type described which is simple to use and safe in its application.

Briefly, a preferred embodiment of the present invention includes a low-voltage power supply, hardware including a microprocessor, a signal generator controlled by the microprocessor, and a pair of probes for making electrical contact to the body. In addition, suitable software is provided for enabling the microprocessor to control operation of the system. In accordance with this embodiment, voltages at a predetermined level are applied to the probes at oscillating frequencies which periodically change from a frequency of approximately 70 kHz at the low end to approximately 880 kHz at the high end in steps of approximately 1 kHz. Preferably, this system is programmed to repeat the cycle several times with brief respites between each cycle.

An important advantage of the present invention is that it enables a user to self-administer treatment to his body at convenient times and outside of a clinical environment.

Another advantage of the present invention is that application of the treatment using the present invention requires almost no training, is inexpensive and can be repeated as often as necessary to achieve a desired result.

Still another advantage of the present invention is that its use is not habit-forming nor in any way threatening to the health of the user.

These and other objects and advantages of the present invention will no doubt become apparent to those skilled in the art after having read the following detailed description of a preferred embodiment which is illustrated in the several figures of the drawing.

DETAILED DESCRIPTION OF THE PREFERRED EMBODIMENTS

Figure 1:
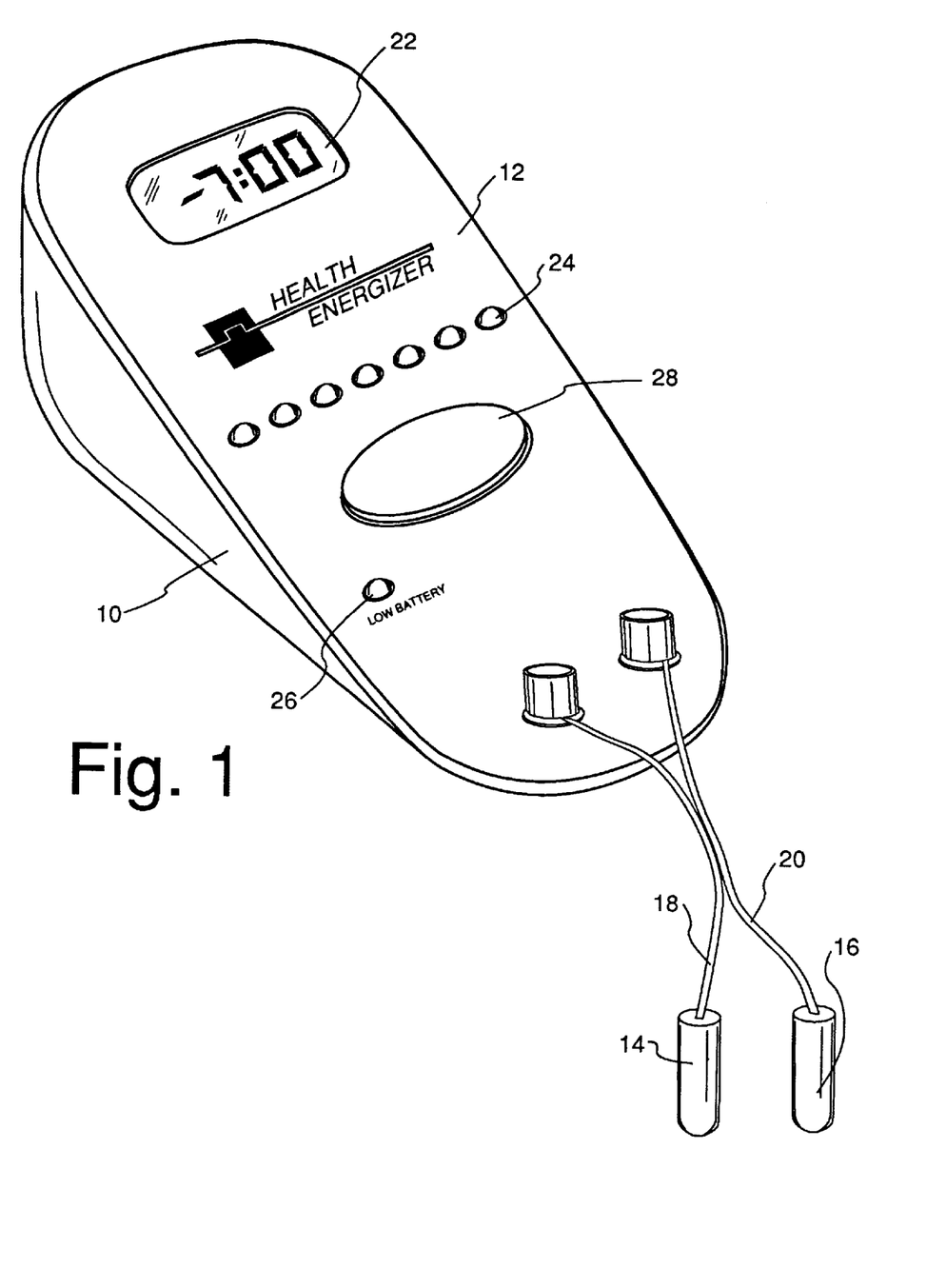
FIG. 1 is a perspective view illustrating a health energizer apparatus in accordance with the present invention.

Turning now to FIG. 1 of the drawing, a "health energizer" apparatus in accordance with the present invention is shown at 10, and includes a free-standing or hand-held unit 12 containing the device electronics and user interface means, and a pair of user contacting electrodes 14 and 16 connected to unit 12 by wires 18 and 20, respectively. The functional components of unit 12 are preferably contained within a suitable housing made of metal or plastic or other appropriate materials, and include a seven-segment LCD display 22, seven light-emitting diodes 24, and an eighth light-emitting diode 26 for indicating battery status. A push button 28 enables a user to turn the device ON, and subsequently signal the start of a therapy cycle.

The electrodes 14 and 16 may take any suitable form capable of conducting electrical energy to the body of a user. As illustrated, the electrodes 14 and 16 are in the form of stainless steel cylinders normally intended to be held in the hands of the user so that electrical energy passes first through one arm, the torso, and then the other arm of the user.

Figure 2:
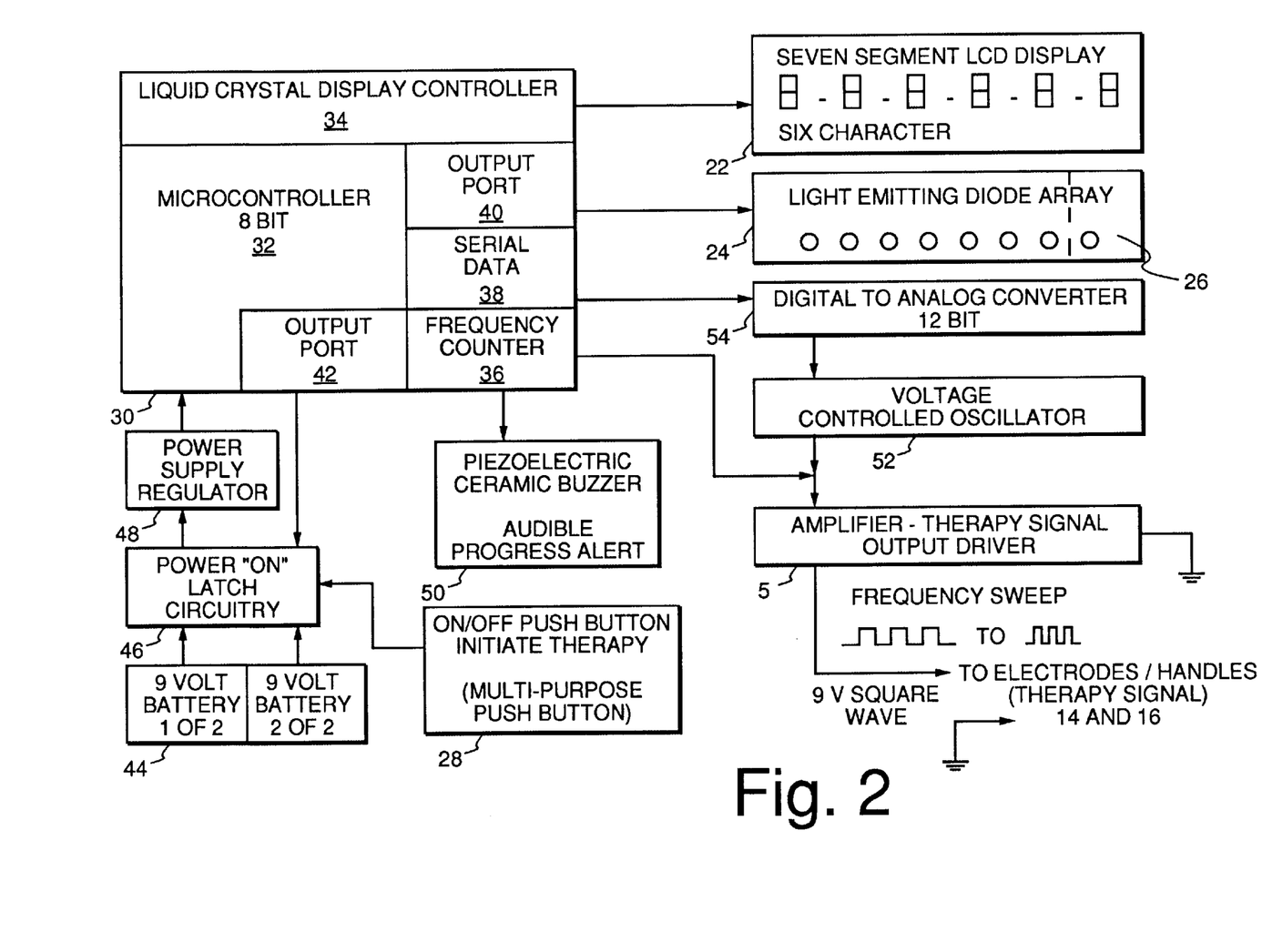
FIG. 2 is a block diagram illustrating the principal functional components of the apparatus depicted in FIG. 1.

In FIG. 2 of the drawing, a functional block diagram illustrates the principal operative components included within the unit 12. The heart of the apparatus is a central processing unit (CPU) 30 including an eight-bit microcontroller 32, an LCD controller 34, a frequency counter 36, a serial data port 38, and a pair of output ports 40 and 42. Power is supplied to CPU 30 from a pair of nine-volt batteries 44 via a power "ON" latch circuit 46 and power supply regulator 48. The multi-purpose push button 28 depicted in FIG. 1 is indicated by the block 28 in FIG. 2. A piezo-electric ceramic buzzer 50 provides an audible progress alert for the apparatus.

The seven-segment LCD display 22 of FIG. 1 is also designated 22 in FIG. 2 and, as illustrated, is capable of displaying six seven-segment characters for displaying status information to the user. The light-emitting diode array 24 also bears the same number of LCDs as in FIG. 1 and forms seven parts of an eight-LED array of which the eighth LED is used as the low-battery indicator 26 shown in FIG. 1. The principal functional output of the apparatus is provided by a voltage-controlled oscillator 52 that responds to the output of a digital-to-analog converter 54 that receives digital input from the serial data port 38 of CPU 30. The output of oscillator 52 is amplified by a power amplifier 56, the output of which is connected to one of the electrodes 14, 16, the other electrode being connected to device ground. The output developed by oscillator 52 is also input to frequency counter 36 to provide closed-loop control of the device operation.

Figure 3:
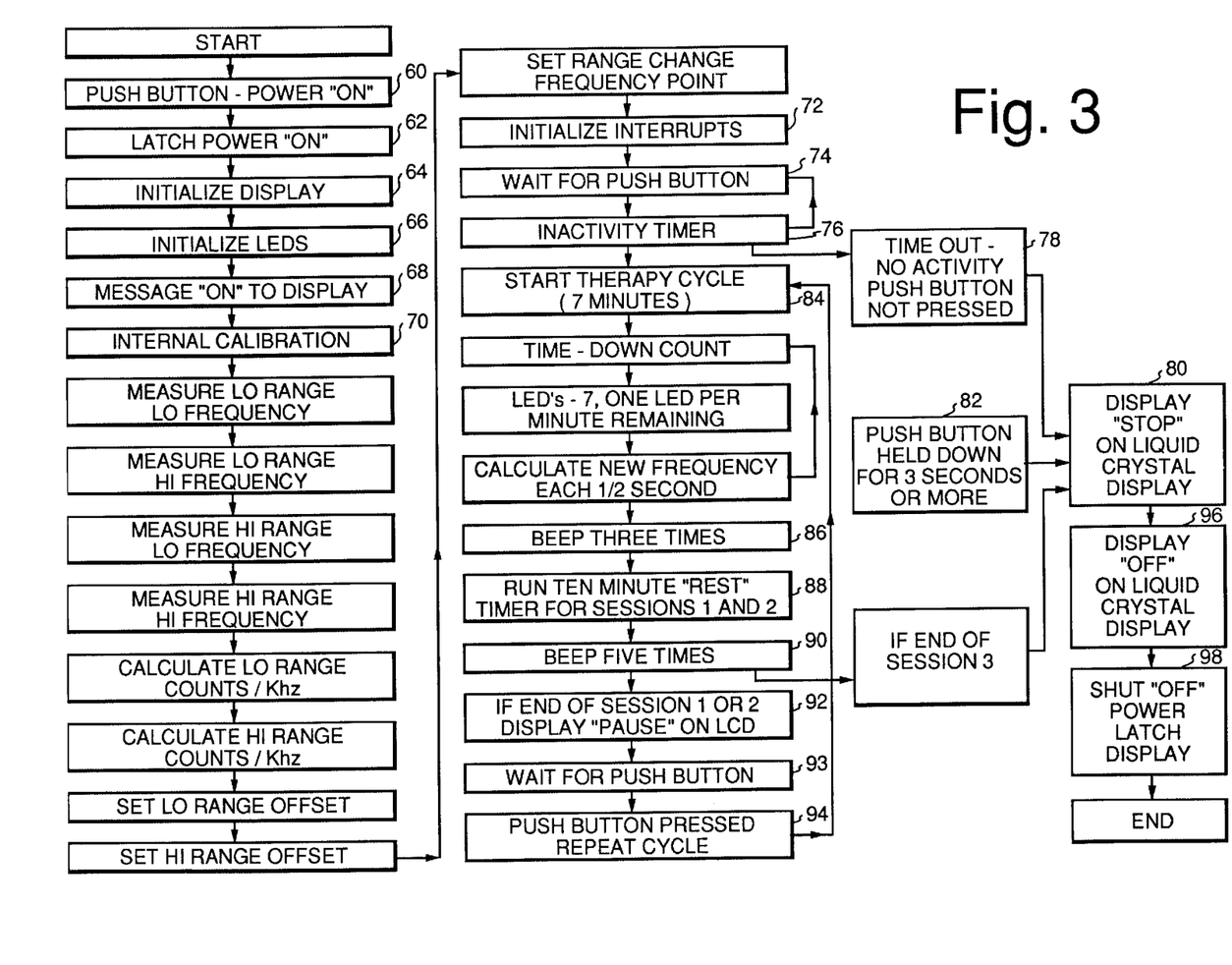
FIG. 3 is a logic flowchart depicting the principal operative steps followed during operation of the apparatus of FIGS. 1 and 2.

In FIG. 3 of the drawing, a flowchart is provided illustrating the operational sequence followed by the apparatus 10. In order to start operation of the apparatus, the user pushes button 28 turning power "ON" as indicated at 60, and latch circuitry 46 latches the power "ON" as indicated at 62. The display 22 and LEDs 24, 26 are then initialized as indicated at 64, 66, and an "ON" signal is displayed in window 22 as indicated at 68. Various internal calibration operations are then carried out as indicated by the block 70 and other blocks appended thereto.

Following the internal calibration, interrupts are initialized as indicated at 72, and the device waits (74) for a second depression of push button 28 to commence operation of the first therapy cycle. As indicated at 76, an internal timer monitors the "wait" state, and if the button 28 is not pushed within a predetermined time interval, the timer will time out indicating no activity, i.e., because the push button 28 was not pressed as indicated by block 78, and the display 22 will be caused to display a "STOP" signal as indicated at 80.

Figure 4:
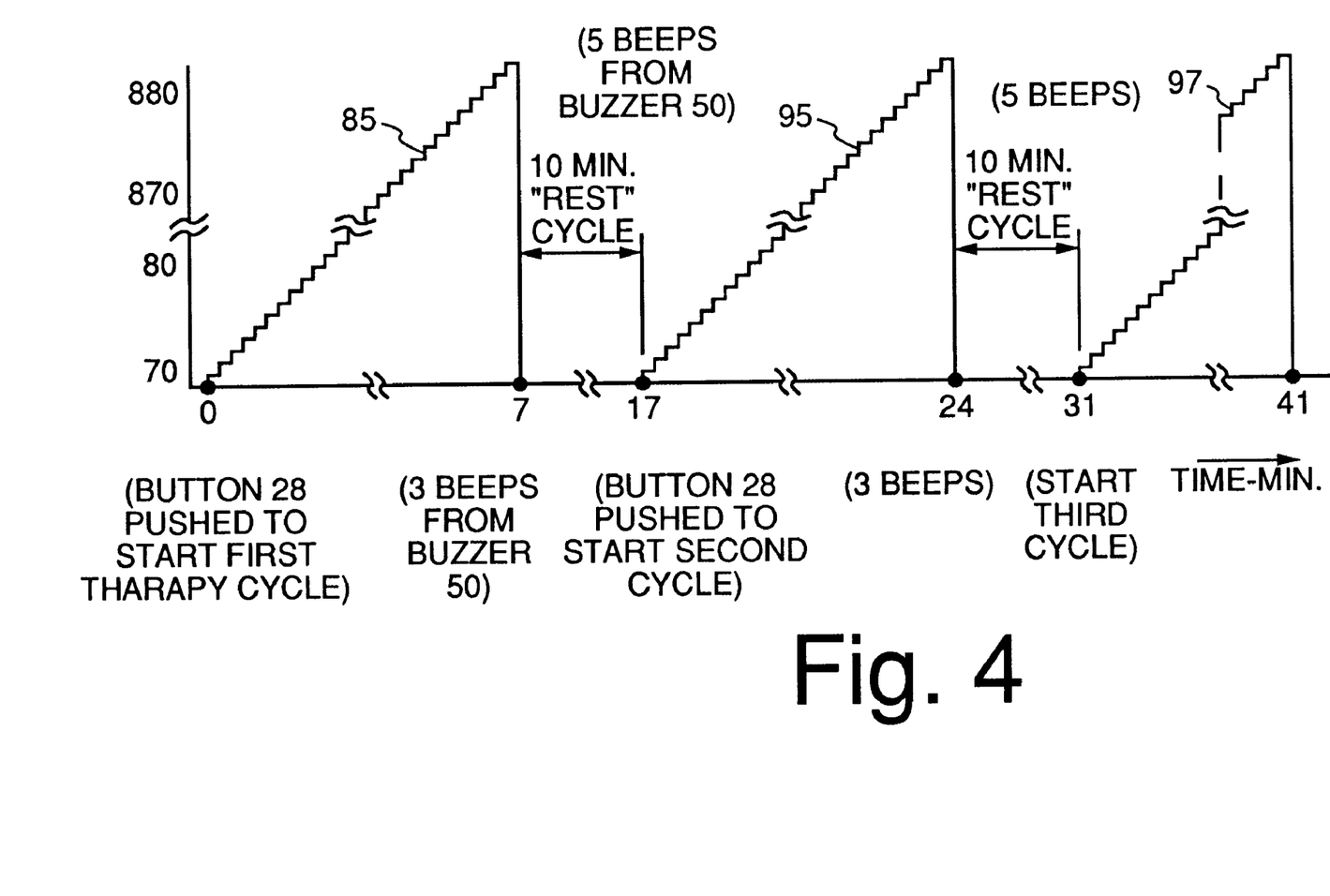
FIG. 4 is a timing diagram illustrating stepped frequency changes and pause periods during operation of the preferred embodiment.

Operation of the device can be stopped at any time by pushing button 28 down and holding it for three seconds or more as indicated at 82. But if push button 28 is pushed before the inactivity timer times out, a first seven-minute therapy cycle will be commenced as indicated at block 84. Following commencement of the cycle, the apparatus 10 will generate a nine-voltage square-wave output for application to electrodes 14, 16, starting at a first frequency (such as, for example, 70 kHz) and at half-second intervals will shift the frequency up 1 kHz until (in approximately seven minutes) the output will have a frequency of approximately 880 kHz. (See timing diagram segment 85 in FIG. 4.) At this time, i.e., seven minutes after start of the first cycle, the audible progress alert buzzer 50 will beep three times (as signified by block 86), the output to electrodes 14, 16 will cease, and a ten-minute "REST" cycle will be commenced (as indicated at 88). At the end of the ten-minute rest period, the buzzer 50 will beep five times (block 90), the system will display "PAUSE" on the LCD display 22 (as indicated at 92), and the system will again wait (93) for the user to push button 28.

If button 28 is pushed (as indicated at 94), operation will revert back to block 84 and a second seven-minute therapy cycle will be commenced, again outputting nine volt pulses initially at a 70 kHz rate, stepping up in frequency by 1 kHz at approximately half-second intervals for the next seven minutes (see segment 95 in FIG. 4), at which time the output to electrodes 14, 16 will again be terminated. The buzzer 50 will again beep three times (block 86), and a second ten-minute "REST" cycle (block 88) will be commenced, followed by five beeps of buzzer 50 (block 90), and a display of "PAUSE" on LCD 22 will again be presented to await a cycle-starting depression of push button 28.

Upon subsequent depression of button 28, a third therapy cycle (see segment 97 in FIG. 4) will be conducted that is identical to the first and second cycles, again followed by three beeps, a ten-minute rest period, the end of which is signified by five beeps from buzzer 50. However, this time the LCD is caused to display "STOP" (80) followed by "OFF" (96) at which time the power latch circuit 46 will be disabled (98) and the therapy session terminated.

Figure 5A:
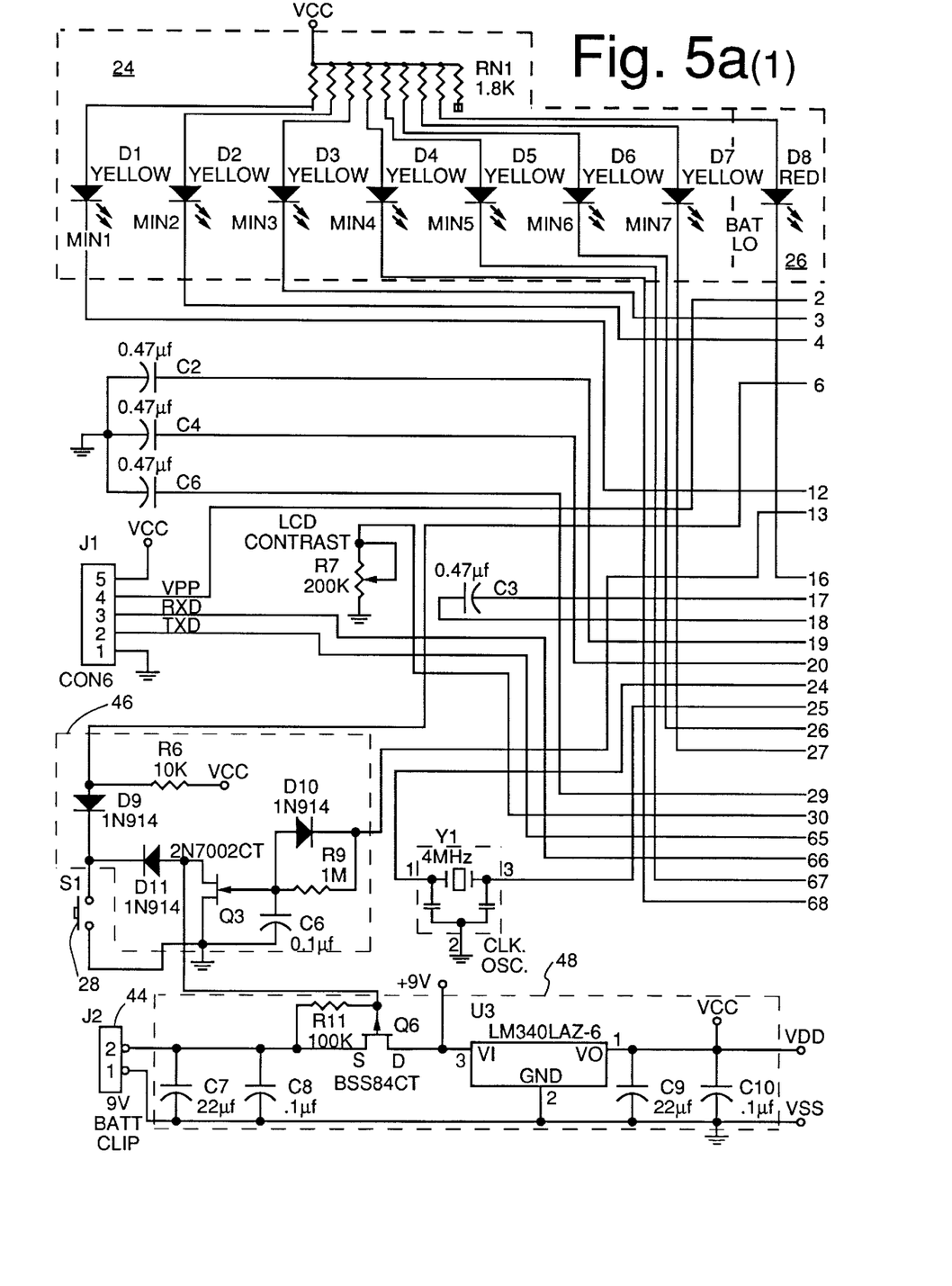
FIGS. 5a and 5b depict a schematic diagram of an actual implementation of the present invention.
Figure 5B:
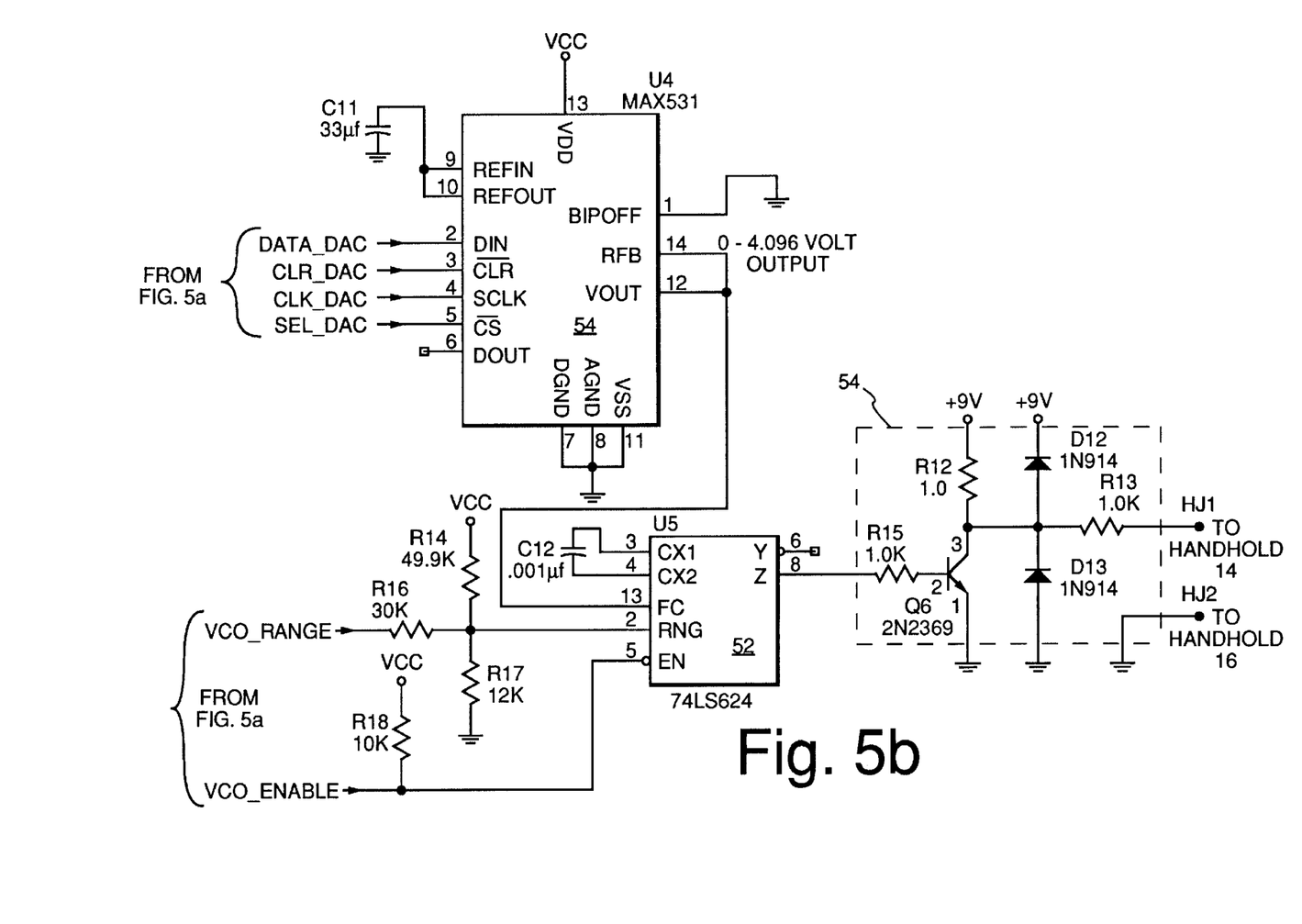

In FIGS. 5a and 5b, an actual schematic implementation of the circuit illustrated in block diagram form in FIG. 2 is illustrated with like call-out numbers being used to signify corresponding subcircuits.

Confirmation of the efficacy of the present invention may be made by first analyzing a particular human subject with a Mora Therapy System to determine the inflammation or degeneration of various organs in the subject's body. This is accomplished using a highly sensitive probe, i.e., a "sender" applied to the subject's body, and an electrode held by the subject to complete a continuity path for current measurements taken along various meridian lines. Measurements made by the system will reflect the general condition of the specific organs addressed. Those that are measured out of a safe normal range are subsequently investigated with respect to a sequence of pathogens that are typically recognized as a causative agent of various conditions. As these are identified in the same manner that the general organ test is performed, the Mora System reading will indicate the presence, or lack of presence, of any number of pathogens as each organ is tested. Those pathogens that are present during the test are noted on a printout along with the time and date of the test.

After a number of pathogens have been identified and categorized, the subject submits to a therapy session using the preferred embodiment of the present invention for the three-cycle preprogrammed test sequence described above, namely: three seven-minute applications of stepped-frequency signals, with each cycle being interrupted by a ten-minute rest period. As the subject experiences the energizer treatment, many of the pathogens detected by the Mora System will be excited and ultimately caused to self-destruct and thus be eliminated. After a predetermined waiting period of approximately twenty minutes, the subject is again subjected to the same Mora System test to again identify remaining active pathogens. Those pathogens that are detected are noted, and the subject is again treated with the health energizer followed by a subsequent Mora System test, and so forth, until substantially all of the pathogens in the subject's body are eliminated.

Although as described above the present invention is adapted to automatically step up, or perhaps down, in frequency in 1 kHz increments from one end of a particular frequency range to another, it is anticipated that there may be applications in which it is more desirable to step between particular frequencies known to excite particular human body pathogens, skipping over those frequencies not known to correspond to particular pathogens. Moreover, where a particular pathogen is known to respond to frequencies within a range of frequencies, it may be desirable to step between multiple frequencies within that range as part of the overall stepping sequence. Note, for example, that no known pathogens are identified in "The Cure for All Diseases" cited above as responding to frequencies within the range of 100 kHz to 126 kHz. It may thus be desirable to cause oscillator 52 to step immediately from the 100 kHz frequency to the 126 kHz frequency. On the other hand, it will be noted in Appendix A that the pathogen *diplococcus diphtheriae* responds to frequencies in the range of 357 kHz to 364 kHz.

In attempting to excite and dispose of this particular pathogen, it may be desirable to step in 1 kHz (or even sub kHz) intervals from 357 to 364 kHz. Note, however, that many other pathogens also respond within this range, so it would not be necessary to particularly tailor the stepping sequence to accommodate excitation of this particular pathogen. This is, of course, true with regard to numerous ones of the pathogens listed in Appendix A.

Although it has been suggested above that one-kHz frequency step increments are desirable and that the same voltage is applied at each frequency step, it is anticipated that for some applications it may be desirable to program the apparatus to step at frequencies other than 1 kHz per interval, and similarly it may be desirable to modulate or otherwise vary the applied voltages at particular frequency applications.

It is also anticipated that, in a more sophisticated embodiment of the present invention, means may be provided for recording or analyzing in real time any variation in current flow through the subject's body with respect to a particular frequency and applied voltage. Such measurements may serve as an aid in identifying the presence of particular pathogens as well as serving to rid the body of such pathogens.

Although the present invention has been described above in terms of specific embodiments, it is anticipated that alterations and modifications thereof will no doubt become apparent to those skilled in the art. It is therefore intended that the following claims be interpreted as covering all such alterations and modifications as fall within the true spirit and scope of the invention.

What is claimed is:

1. A method of eliminating deleterious pathogens within the body of a human subject, comprising the steps of:

generating a series of oscillating voltage levels oscillating at fixed frequencies for predetermined intervals of time and stepping in frequency during successive intervals of time over a range of frequencies varying from approximately 70 kHz to approximately 880 kHz; and applying the oscillating voltage across a portion of the body of a subject causing a corresponding oscillating current flow to pass through the body of the subject to excite pathogens present within the subject's body and cause their neutralization or destruction.

2. A method as recited in claim 1 wherein, following application of said oscillating voltage pulses to the subject's body, the voltage application is terminated for a predetermined period of time, followed by a subsequent repeat of the oscillating and stepped-frequency voltage application.

3. A method as recited in claim 2 wherein, following said second application of voltages to the body of the subject, a second rest period free of the application of voltages is observed, followed by a third application of the alternating voltages.

4. Apparatus for treating pathogens within a human body, comprising:

a pair of conductive electrodes adapted to conductively engage physically separated points on the body of a human subject;

signal-generating means for generating an oscillatory signal varying between a first voltage level and a second voltage level at frequencies within the range of 70 kHz to 880 kHz;

means for causing said signal-generating means to step in frequency from one extreme to another of said range at predetermined frequency steps for predetermined intervals; and power-amplifying means responsive to said stepped voltage signals and operative to apply corresponding voltage levels across said electrodes.

5. Apparatus as recited in claim 4 and further comprising electronic display means for displaying to the subject indications of the progress of the treatment.

6. Apparatus as recited in claim 4 and further comprising:

electronic signal-processing means for generating a series of digital signals corresponding to each said frequency step;

digital-to-analog converter means responsive to said digital signals and operative to generate corresponding analog voltage levels;

voltage-controlled oscillator means responsive to said corresponding voltage levels and operative to generate a pulse train oscillating at a frequency corresponding to said corresponding voltage level; and power-amplifying means responsive to said pulse train and operative to apply pulsating voltages across said electrodes.

7. Apparatus as recited in claim 6 wherein said voltage-controlled oscillating means generates square-wave pulses for amplification by said power-amplifying means.

8. Apparatus as recited in claim 7 wherein said controller means includes frequency-counting means responsive to the output of said voltage-controlled oscillator and operative to generate a count signal from which said controller controls the frequency thereof.

9. Apparatus as recited in claim 4 wherein a single ON-OFF push button is combined with latch circuitry and operative, upon each closure thereof, to cause a different function of the circuit to be initiated.

10. Apparatus as recited in claim 9 and further comprising audible enunciator means for indicating the progress of operation of said apparatus.

11. Apparatus as recited in claim 4 wherein each said step is chosen to have a frequency corresponding to a frequency within the range of known excitation frequencies of a particular pathogen known to appear in the human body.

* * * * *